(12) United States Patent
Barash et al.

(10) Patent No.: US 10,537,244 B1
(45) Date of Patent: Jan. 21, 2020

(54) USING EYE TRACKING TO LABEL COMPUTER VISION DATASETS

(71) Applicant: Amazon Technologies, Inc., Seattle, WA (US)

(72) Inventors: Benjamin Jack Barash, Seattle, WA (US); Yves Albers Schoenberg, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 66 days.

(21) Appl. No.: 15/695,884

(22) Filed: Sep. 5, 2017

(51) Int. Cl.
*A61B 3/113* (2006.01)
*G06K 9/00* (2006.01)

(52) U.S. Cl.
CPC .......... *A61B 3/113* (2013.01); *G06K 9/00597* (2013.01); *G06T 2207/30201* (2013.01)

(58) Field of Classification Search
CPC ..... A61B 3/113; A61B 3/0033; A61B 5/1114; G06K 9/00597; G06K 9/00711; G06K 9/00771; G06K 9/34; G06T 2207/30201; G06F 3/013; G06F 3/012; G06F 3/167; G06F 3/0482; G06F 3/04842; G06F 1/3231; G06F 2203/0381; G06Q 30/0241; G10L 15/08; G10L 15/00; G10L 15/02

USPC .................................. 351/209, 246; 704/275
See application file for complete search history.

(56) References Cited

U.S. PATENT DOCUMENTS

| | | | |
|---|---|---|---|
| 8,879,155 B1* | 11/2014 | Teller | G06K 9/00604 359/630 |
| 9,317,113 B1* | 4/2016 | Karakotsios | G06F 3/013 |
| 2016/0091967 A1* | 3/2016 | Prokofieva | G06F 3/012 345/156 |
| 2018/0024633 A1* | 1/2018 | Lo | G06F 3/0482 345/156 |
| 2018/0233141 A1* | 8/2018 | Solomon | G06K 9/726 |

* cited by examiner

*Primary Examiner* — Collin X Beatty
(74) *Attorney, Agent, or Firm* — Lee & Hayes, P.C.

(57) ABSTRACT

A system is configured to label computer vision datasets using eye tracking of users that track objects depicted in imagery to label the datasets. The imagery may include moving images (e.g., video) or still images. By using eye tracking, users may be able to label large amounts of imagery more efficiently than by manually labeling datasets using conventional input devices. A user may be instructed to watch a particular object during a playback of the video while an imaging device determines a direction of the user's gaze which correlates with a location in the imagery. An application may then associate the location in the imagery determined from the user's gaze as a location of the object on a frame-by-frame basis, or for certain frames.

20 Claims, 8 Drawing Sheets

USING EYE TRACKING TO LABEL COMPUTER VISION DATASETS

BACKGROUND

In order to train computer vision algorithms, researchers must acquire a large amount of manually labelled data sets. The labelled data sets serve as a ground truth during an algorithm training process and essentially teach the algorithm what to look for in imagery included in the dataset. Accurate labelling is vital to a trained model's inference ability on new, unseen data.

However, the acquisition of labelled data, especially for novel environments and contexts, is extremely time consuming. Researchers either manually label the data themselves (frame by frame) or outsource the work to third party contractors. In the latter case, if the data is confidential or sensitive, this is usually not an option.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

This disclosure is directed to labeling computer vision datasets using eye tracking of users that track objects depicted in imagery to label the datasets. The imagery may include moving images (e.g., video) or still images. By using eye tracking, users may be able to label large amounts of imagery more efficiently than by manually labeling datasets using conventional input devices, such as a mouse or other tracking device, a keyboard, or a touch screen, thereby optimizing use of computing hardware. In some embodiments, the labeling may be performed using a video that includes multiple frames of images.

A user may be instructed to watch a particular object on the display during a playback of the video while a camera or other imaging device may determine a direction of the user's gaze which correlates with a location in the object in the imagery. An application may then associate the location in the imagery determined from the user's gaze as a location of the object on a frame-by-frame basis, or for certain frames. In some embodiments, the location of the object in the imagery determined by the user's gaze may be a relatively small region of interest (ROI), which may be associated with a group of pixels that only create part of the object. The application may use image analysis application, such as an edge detection algorithm to create a bounding shape around the object. The bounding shape may be associated with the location of the object on a frame-by-frame basis, or for certain frames.

In some embodiments, names or labels of the objects to be tracked by eye movement of users may be predetermined. However, users may be prompted to identify objects and label the objects depicted in imagery. In various embodiments, a user may view the imagery or a portion of the imagery (e.g., some frames of a video, etc.) and may label the objects shown in those frames. For example, the user may be prompted to announce all the objects shown in the imagery or certain types of objects (e.g., objects that may interfere with an aircraft, etc.). The system may capture the labels of the object via voice recognition of speech captured as signals by one or microphones. The system may capture the labels using other input devices, such as input of text via a keyboard. At a later time, the user may then be prompted to track at least some of the objects identified during the labeling process to determine locations of those objects in the imagery. In some embodiments, the user may announce an object he or she is looking at, which may act to label the object and trigger a time to determine a location of the object via eye tracking of a gaze of the user.

In accordance with one or more embodiments, an input device may be used to receive input from a user that is tracking objects in the imagery. The input may indicate that the user is currently tracking an object in the imagery by the user's gaze. The input or a different input may indicate that the tracking has terminated, such as when the user loses focus, needs a break, etc. or when the object leaves the field of view in the imagery or is concealed by another object in the imagery (e.g., the airplane goes behind a cloud and is temporarily not visible in the imagery). Thus, one or more input devices may be used to indicate a start of tracking, an end of tracking, a pause in tracking, a request for new imagery, a rewind of the imagery to re-track the object, and/or for other reasons. In some embodiments, when imagery is played back, the first few frames may not be labeled to provide time for the user to set her gaze upon a particular object. For example, the system may instruct a user to watch and track movement of a bird in a video. When the video starts playback, the user's eyes may scan across the imagery to locate the bird during the first frames shown to the user. The eye gaze tracking of these frames may be disregarded due to this initial scanning by the user to find the object (the bird) before tracking of the object begins. The scanning may be assumed to have a predetermined duration, predetermined number of frames, or other predetermine length or metric.

During tracking of an object, the user's gaze may, from time to time, momentarily lose focus from the object to be tracked or may otherwise deviate from an actual location of the object depicted in the imagery. For example, the user may become tired and her eyes may drift away from the object at times. As other example, the user may cough, sneeze, or make other movements that temporarily cause the user gaze to move away from the object. To avoid incorrect labeling of object during these frames, the location of the object determined by the eye tracking of the eye gaze may be compared to a location of the object determined by an object tracking algorithm. The object tracking algorithm may rely on at least some of the eye tracking data to determine an initial location of the object for tracking purposes. When a variance between the object location determined by the eye gaze (which may at times lose focus on the object) and the object location via the object tracking algorithm is greater than a predetermined threshold, the application may initiate a correction process to correct frames that may otherwise be mislabeled if the object location were solely based on the eye tracking. The correction may be to replay the imagery for another eye tracking by the user, to use the object location of the object tracking algorithm, mark corresponding frames as unlabeled, or the correction may include other processes.

As indicated above, user behavior may be monitored by the eye tracking and/or by general input received by the user via a microphone, cameras or imaging devices used for eye tracking of the eye gaze, and/or other sensors. Certain occurrence of user behavior may indicate a poor quality of the labeling of data or may otherwise impact the quality of the labeling, such as by indicating that the location of the eye gaze may not have a strong correlation with a location of the object depicted in the imagery. For example, when the user is tired, the user may lose focus of the object, undergo prolonged blinking and/or otherwise lose focus on an object from time to time. In addition, reflex action such as coughing, yawning, sneezing, and/or other reflex actions may indicate that the eye tracking location may not correlate with the location of the object depicted in the imagery for at least some frames. In some embodiments, an imagery presenter may be informed by user behavior and may replay some imagery based on occurrence of certain behavior, may change imagery based on certain behavior, and/or may terminate a labeling session based on certain behavior or for other reasons such as when the session time has elapsed.

The techniques and systems described herein may be implemented in a number of ways. Example implementations are provided below with reference to the following figures.

Figure 1:
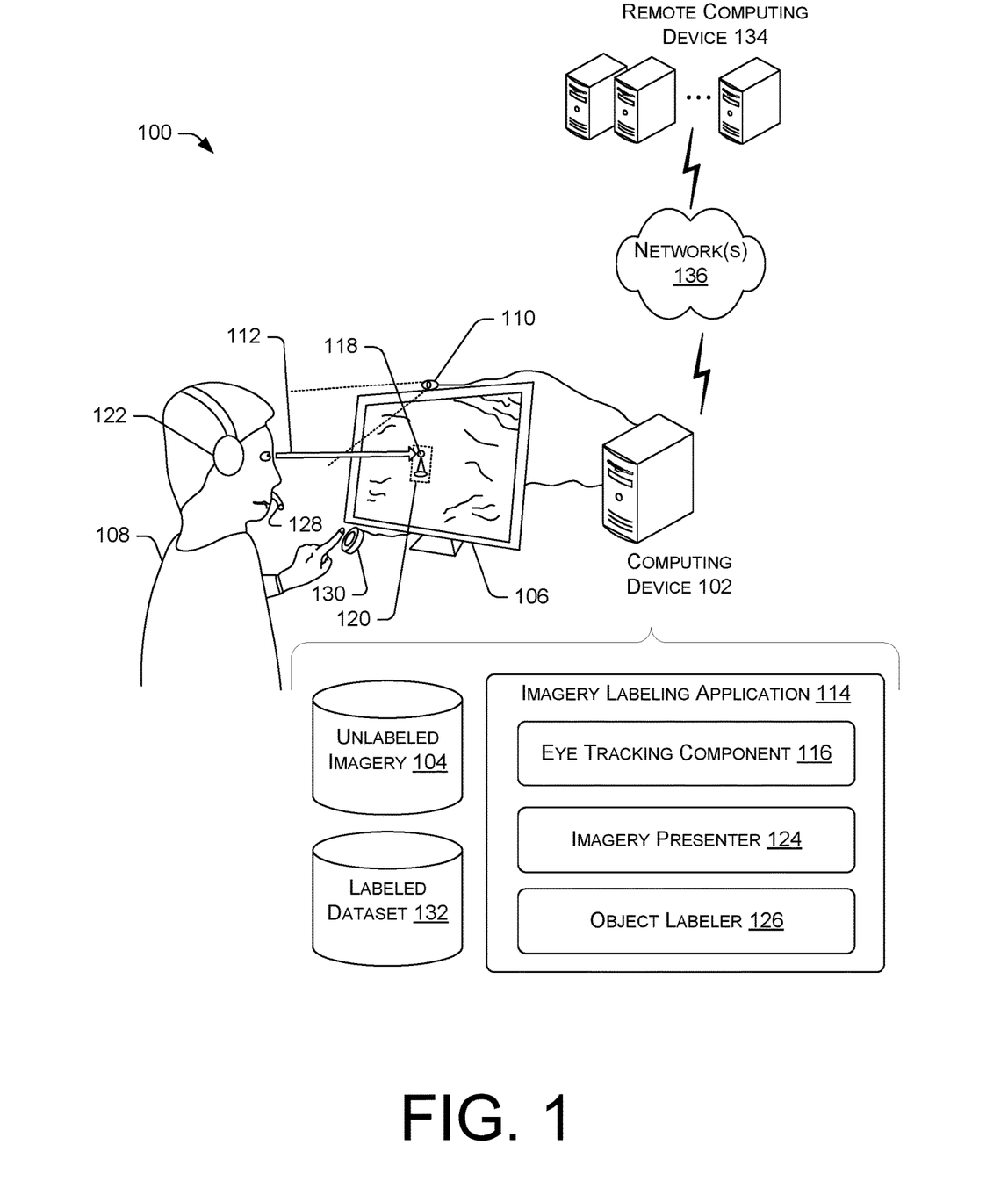
FIG. 1 is a schematic diagram of an illustrative environment configured to use eye tracking to label computer vision datasets.

FIG. 1 is a schematic diagram of an illustrative environment 100 configured to use eye tracking to label computer vision datasets. The environment may include a computing device 102 that may facilitate playback of imagery for labeling using eye tracking data that locates objects depicted in the imagery based on a location associated with a gaze of a user's eye or eyes. The computing device 102 may output imagery from unlabeled imagery 104 to a display 106 for viewing by a user 108. The computing device may be coupled to a one or more imaging devices 110 (e.g., a camera) that are used to track at least a gaze 112 of eyes of the user 108. For example, the computing device 102 may include an imagery labeling application 114 that includes an eye tracking component 116 that uses one or more eye tracking algorithms that process the imagery from the imaging devices 110 to determine a location 118 of the display 106 that is being viewed by the user 108. This location 118 may correlate with a location of a certain object 120, such as an object that the user 108 is instructed to track (watch) while viewing the imagery. For example, the computing device 102 may cause a speaker 122 to output a command or instruction of a task for the user 108. The imaging sensors 110 may include a projector to project light on the user's eyes, such as near infrared light, which may be used by the imaging sensors 110 to better detect the user's gaze 112. Eye tracking algorithms may be provided by Tobii® of Sweden or other providers of eye tracking algorithms.

The computing device 102 may include an imagery presenter 124 and an object labeler 126 as part of the imagery labeling application. The imagery presenter 124 may select imagery from the unlabeled imagery 104 to present to the user 108 via the display 106. The imagery may be still imagery, moving imagery (e.g., video), or a combination of both. In some embodiments, the imagery presenter 124 may replay at least some portions of the imagery to the user 108 or to other users to increase an accuracy of object location determined from the gaze 112 of the user and/or from other users tracking the object in the imagery using similar systems.

The object labeler 126 may determine objects in the imagery to be tracked. In some embodiments, the object labeler 126 may prompt the user 108 to identify objects depicted in the imagery shown on the display 106. For example, the user 108 may announce (speak) the names of objects shown in the imagery, which may be received by the computing device 102 via a microphone 128 and processed by the object labeler 126. The object labeler 126 may associate a name or label with an object, which may then be associated with a location of the object determined by the eye tracking component 116 as discussed in greater detail below. This data may be stored as labeled data 132, which may include the imagery or may be metadata associated with the imagery stored in the unlabeled imagery 104.

In various embodiments, the computing device 102 may be in communication with one or more input devices 130. The input devices 130 may include a keyboard or a subset of a keyboard. The input devices 130 may be specialized button or input that allows the user to provide feedback to the computing device 102 and to the imagery labeling application 114, such as to initiate playback of on object, indicate when the user is tracking on object, indicate that the object is in the field of view of the imagery, and/or for other reasons.

In some embodiments, the computing device 102 may be in communication with one or more remote computing device(s) 134 via one or more network(s) 136. The network(s) 136 may be wired networks, wireless networks, or a combination of both that facilitate an exchange of data between computing devices. The remote computing device(s) 134 may include other computing devices that perform a same or similar function as the computing device 102 to facilitate labeling of imagery by other users. The remote computing device(s) 134 may coordinate and/or aggregate labeling of data of multiple users, such as the user 108 that interacts with the computing device 102. The computing device(s) 134 may provide some resources, components, modules, and/or other data to assist the computing device 102 or as part of a distributed system that includes the computing device 102. For example, the computing device 102 may send audio information captured by the microphone 128 to the remote computing device(s) 134 for automated speech recognition to determine text labels for objects depicted in the imagery. Of course, the remote computing device(s) 134 pay perform other computing services for the computing device 102 or in conjunction with the computing device as discussed herein.

Figure 2:
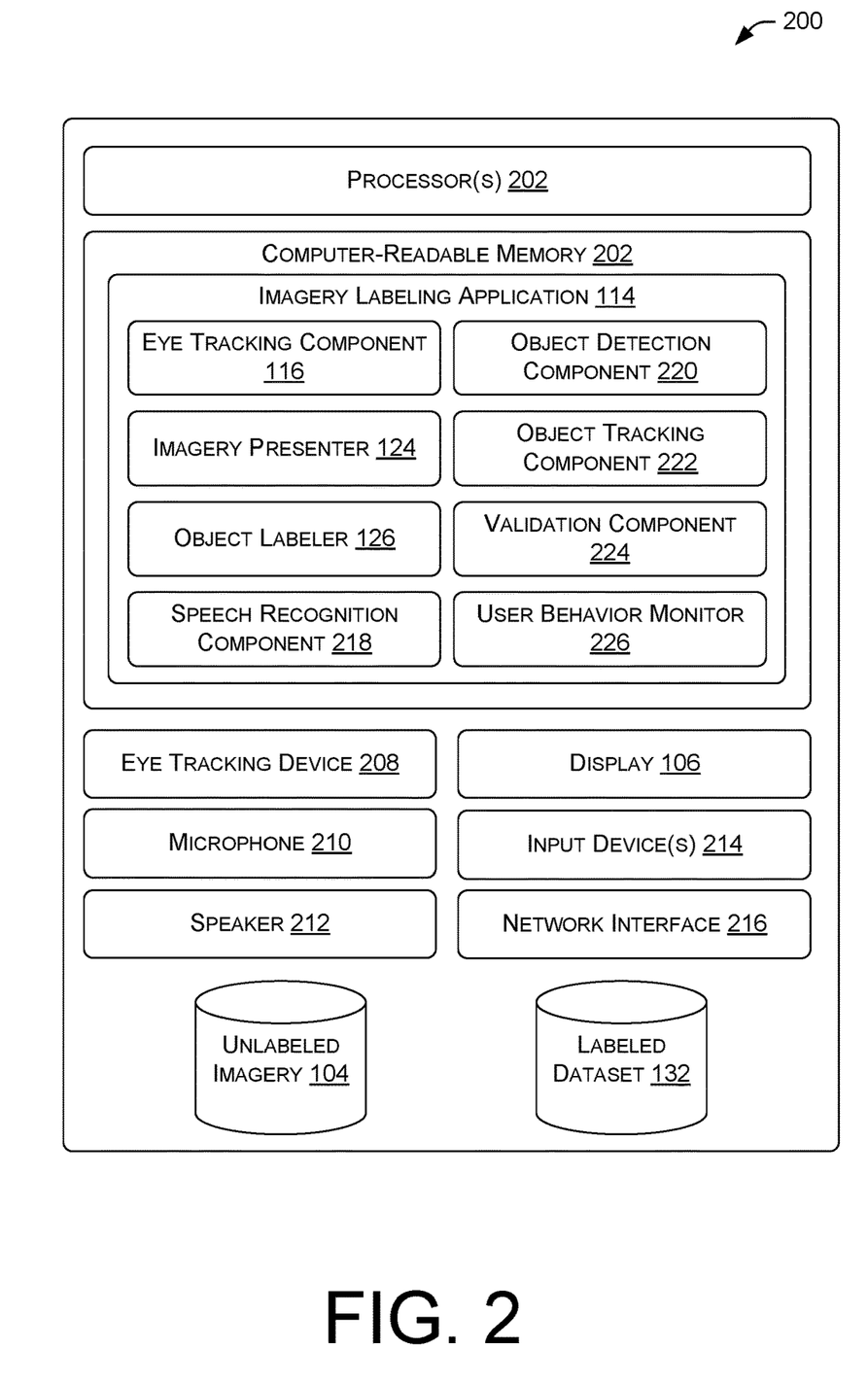
FIG. 2 is a block diagram of illustrative computing architecture shown in FIG. 1.

FIG. 2 is a block diagram of illustrative computing architecture 200 shown in FIG. 1. The computing architecture 200 may be implemented in a distributed or non-distributed computing environment.

The computing architecture 200 may include one or more processors 202 and one or more computer readable media 204 that stores various modules, applications, programs, or other data. The computer-readable media 204 may include instructions that, when executed by the one or more processors 202, cause the processors to perform the operations described herein.

The computing architecture 200 may include an eye tracking device 208 that may provide functionality and provide signals for use by the eye tracking component 116. The eye tracking device 208 may include at least one projector to project light patterns toward a head of a user viewing the display 106. The projector may emit infrared or near infrared light to illuminate eyes of the user, such as the retina. The eye tracking device 208 may include one or more imaging devices (e.g., image sensors, cameras, etc.) to capture signals indicating a position of the eye using the patterns. The imaging devices may capture information about the position of the eyes and parts of the eyes, reflection patterns, and/or other information to enable a determination of a direction of a gaze of the user at a point in time correlated with playback of imagery on the display 106 via the imagery presenter 124.

The computing architecture 200 may include a microphone 210 to receive voice input from a user, such as the user 108 shown in FIG. 1. For example, the user may speak commands, announce an action the user is performing (e.g., "tracking a bird", etc.), label objects depicted in imagery, and/or capture other audio commands or information announced (spoken) by a user. In some embodiments, the signals generated by the microphone may be analyzed by automated speech recognition (ASR) algorithms and/or natural language processing (NLP) algorithms to determine text commands as inputs to the imagery labeling application.

The computing architecture 200 may include a speaker 212 to emit sounds to provide feedback to a user, provide instructions to a user, and so forth. For example, the speaker 212 may be used to emit sounds to instruct the user to label objects of a specified type that are depicted in the imagery. The speaker 212 and the microphone 210 may be implemented separately or may be combined (e.g., in a headset, etc.) and may be in wired or wireless communication with the computing device 102 shown in FIG. 1.

The computing architecture 200 may include one or more input device(s) 214 to receive user input. The input device(s) 214 may include a keyboard or a subset of a keyboard, or may be implemented as a special device (e.g., a physical button or set of buttons, etc.). The input device(s) 214 may receive user input that allows the user to provide feedback to the computing device 102 and to the imagery labeling application 114, such as to initiate playback of on object, indicate when the user is tracking on object, indicate that the object is in the field of view of the imagery, and/or for other reasons. The input or continued input (e.g., holding input device down) may indicate that the user is currently tracking an object in the imagery by the user's gaze. The input or end of the input, or a different input, may indicate that the tracking has terminated, such as when the user loses focus, needs a break, etc. or when the object leaves the field of view in the imagery or is concealed by another object in the imagery (e.g., the airplane goes behind a cloud and is temporarily not visible in the imagery). Thus, the input device(s) 214 may be used to indicate a start of tracking, an end of tracking, a pause in tracking, a request for new imagery, a rewind of the imagery to re-track the object, and/or for other reasons.

The computing architecture 200 may include one or more network interface 216. The network interface(s) 216 may enable exchange of data and/or signals via wired networks and/or wireless networks to communication with remote hardware, local hardware, and/or other components. For example, the network interface(s) 216 may enable wireless communication with a microphone and speaker and/or with the remote computing device 134 shown in FIG. 1.

Embodiments may be provided as a computer program product including a non-transitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/ machine-readable medium suitable for storing electronic instructions. Further, embodiments may also be provided as a computer program product including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks. For example, distribution of software may be by an Internet download.

In some embodiments, the computer-readable media 204 may store the imagery labeling application 114 and associated components, such as the eye tracking component 116, the imagery presenter 124, the object labeler 126, a voice recognition component 218, an object detection component 220, an object tracking component 222, a validation component 224, and a user behavior monitor 226, which are described in turn. The components may be stored together or in a distributed arrangement.

The eye tracking component 116 may uses one or more eye tracking algorithms that process the imagery from the imaging devices 110 to determine a location of the display that is being viewed by the user. This location may correlate with a location of a certain object, such as an object that the user is instructed to track (watch) while viewing the imagery. The eye tracking component 116 may output a pixel location and time (or frame) associated with a particular object that is being tracked via the process. In some embodiments, the eye tracking component 116 may analyze a pattern of light emitted on a pupil, cornea, and/or retina, and may determine a direction of a gaze of the user based on that information. The direction of the gaze may be used to determine the pixel location in the imagery. The eye tracking component 116 may be synchronized or in communication with the imagery presenter 124 to associate the pixel location with a frame or time of playback of the imagery when the imagery includes video.

The imagery presenter 124 may select imagery from the unlabeled imagery 104 to present to the user via the display. The imagery may be still imagery, moving imagery (e.g., video), or a combination of both. In some embodiments, the imagery presenter 124 may replay at least some portions of the imagery to the user or to other users to increase an accuracy of object location determined from the gaze of the user and/or from other users tracking the object in the imagery using similar systems. The imagery presenter 124 may by synchronized or in communication with the eye tracking component to enable associating the pixel location with a frame or time of playback of the imagery when the imagery includes video. In some embodiments, the imagery presenter may receive information from the user behavior monitor to determine to change imagery, replay imagery, or terminate a session.

The object labeler 126 may determine objects in the imagery to be tracked. In some embodiments, the object labeler 126 may prompt the user to identify objects depicted in the imagery shown on the display. For example, the user may announce (speak) the names of objects shown in the imagery, which may be received by the computing device via the microphone 210 and processed by the object labeler 126. The object labeler 126 may associate a name or label with an object, which may then be associated with a location of the object determined by the eye tracking component 116 as discussed above. This data may be stored as labeled data 132, which may include the imagery or may be metadata associated with the imagery stored in the unlabeled imagery 104.

The speech recognition component 218 may process some or all of audio received via the microphone 210, such as user commands, user object labels, and/or other speech from a user. In some embodiments, the speech recognition component 218 may perform ASR and/or NLU. However, the speech recognition component 218 may offload at least some processing to a remote computing device, such as the remote computing device(s) 134 shown in FIG. 1 for further processing.

The object detection component 220 may associate the pixel location (also referred to as a region of interest (ROI)) determined by the eye tracking component 116 with a bounding shape or area of the imagery that includes the object in a particular frame of the imagery. The object detection component 220 may use edge detection algorithms and/or other image recognition algorithms to determine the bounding shape or area of the imagery. The bounding shape may be an outline of the object and may not be rectangular, but may include curvature that follows an outline or close to an outline of the object. The output of the object detection component 220 may be stored at part of the data in the labeled dataset 132. The output of the object detection component 220 may also be used to inform the object tracking component 222.

The object tracking component 222 may track an object across images or frames in imagery using at least some information from the object detection component 220. For example, the object tracking component 222 may determine from some user labeling (e.g., via some eye tracking data of one or more frames), that an object in another frame has a certain label. The object tracking component 222 may use a tracking algorithm to determine movement of the object across different frames. This movement of the object may enable comparison and validation of information from the eye tracking component, among other possible uses.

The validation component 224 may analyze at least some of the data from the eye tracking component 116, possibly in comparison to object location information generated by the object tracking component 222, to determine if the location of the object determined by the eye tracking is a correct location of the object. As an example, a user may get distracted during a task to track an object in the imagery and have a lapse where he fails to track the object, but instead drifts his eyes to another location of the display or off the display. As another example, the user may cough, sneeze, yawn, blink, squint, or perform other actions that inhibit the eye tracking component 116 from tracking the gaze of the user or create a gaze that does not follow or track the object. The validation component 224 may determine these events, such as when eye tracking object location data varies from object location generated by the object tracking component 222 by more than a threshold amount. As a result, the validation component 224 may provide information to another component or components, such as the imagery presenter 124, which may initiate replay of imagery, mark certain imagery as not labeled, use the output of the object tracking component to adjust the object location determined by the eye tracking component 116, and/or perform other actions. In some embodiments, the movement of an object associated with eye tracking may be unexpected, even without comparison with other data from the object tracking component 222. For example, the validation component may determine that the object cannot move in certain ways relative to other determined object, which may be used to invalidate some eye tracking data from the eye tracking components 116, such as to indicate that the user failed to properly track the object at certain times or for certain frames. This may be particularly relevant when the object being tracked is constrained by another object already tracked, for example.

The user behavior monitor 226 may determine attributes of a user that tracks the imagery with her eyes to determine information about the user and/or the validity of labeling performed as a result of the tracking. For example, the user behavior monitor 226 may measure eye drift (movements, speed, redirection, etc.), blinking rate and/or duration, and/or other attributes that may indicate sleepiness or fatigue. The user behavior monitor 226 may determine occurrence of a yawn, cough, sneeze, or other physical occurrence that may disrupt obtaining accurate eye tracking of an object for at least some frames. This information may be used to inform the imagery present 124 (e.g., to replay, terminate a session, etc.), and/or may be used to inform the validation component 224 as discussed above.

FIGS. 3-8 are flow diagrams of illustrative processes illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

Figure 3:
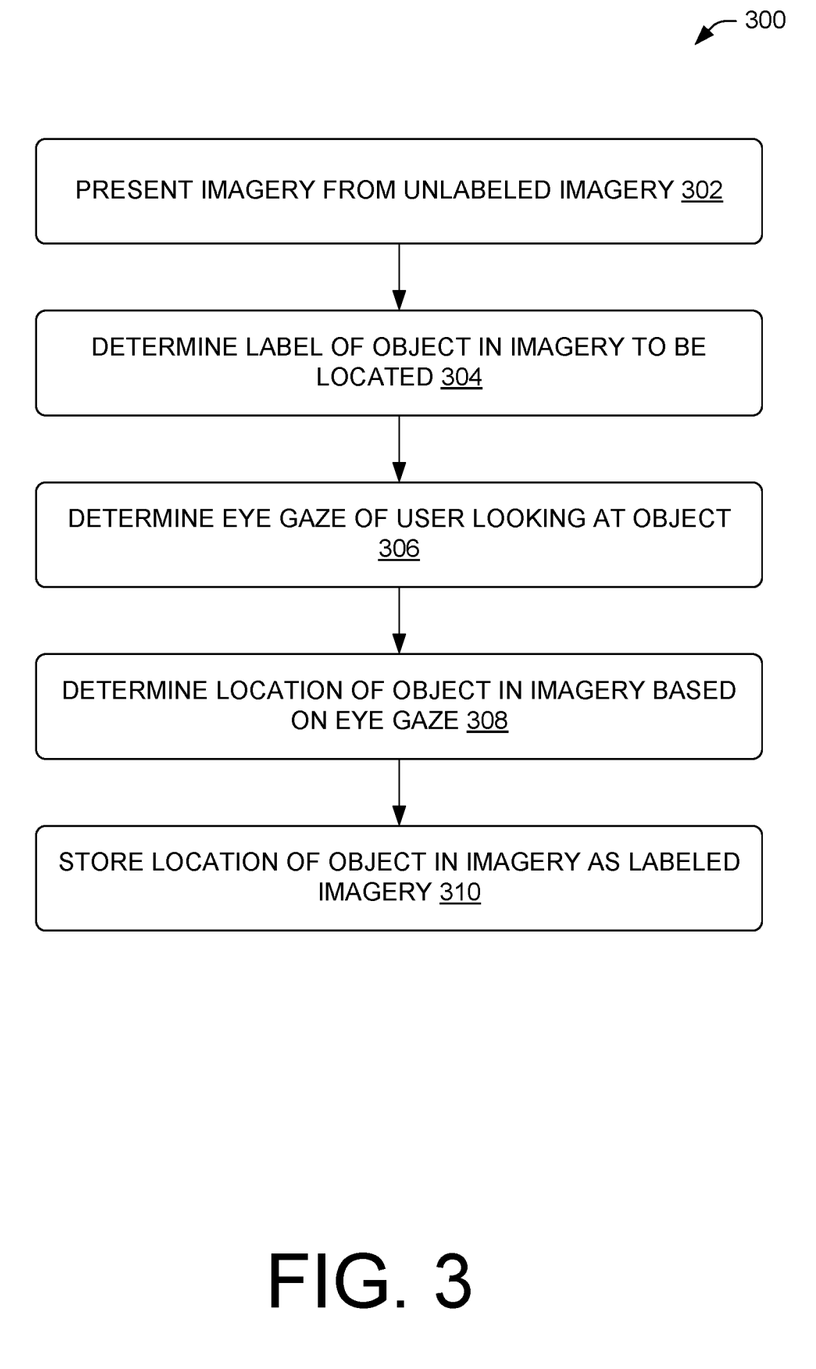
FIG. 3 is a flow diagram of an illustrative process to label location(s) associated with an object depicted in imagery based on an eye gaze of a user looking at the object.

FIG. 3 is a flow diagram of an illustrative process 300 to label location(s) associated with an object depicted in imagery based on an eye gaze of a user looking at the object. The process 300 is described with reference to the environment 100 and the computing architecture 200. However, the process 300 may be performed by other computing architecture and in other environments.

At 302, the imagery presenter 124 may cause a display to present imagery from the unlabeled imagery 104. For example, the imagery presenter 124 may select on image or a series of images (e.g., a video) for playback to a user that is instructed to track an object in the imagery.

At 304, the object labeler 126 may determine the object in the imagery to be labeled and located. In some embodiments, the object labeler 126 may access predetermined labels, such as names of objects depicted in the imagery. For example, an object may be a bird, a tree, an airplane, a vehicle, a person, an animal, and/or other moving or stationary things that can be classified and identified by a user. In some embodiments, the object labeler 126 may determine a label of an object based at least in part on user input. For example, the object labeler 126 may prompt a user to input names of objects depicted in one or more images of the imagery. In some instances, the object labeler 126 may supply a criteria for the object to be named by the user, such as "an object not yet named", "an object that can move", and/or by using other criteria.

At 306, the eye tracking component 116 may determine a direction of a gaze of the user that is tracking the labeled object during presentation of the imagery. For example, the eye tracking component 116 may determine a pixel location of the imagery at a point in time or frame. The eye tracking component 116 may be synchronized with the imagery presenter to enable associating the pixel with the point in time or frame of the imagery when the imagery is video or moving images.

At 308, the object detection component 220 may determine the location of the object in the imager based on the pixel determined by the eye gaze. For example, the eye gaze may determine a pixel, or region of interest (ROI) that include a part of an object (e.g. a face of a person). The object detection component 220 may determine that the ROI is part of a larger object, and may determine bounds for the larger object, such as by defining a bounding shape or box that at least partially surrounds the object. The object detection component 220 may determine the object location for each frame using inputs from the eye tracking component 116.

At 310, the image labeling application 114 may store the location of the object determined at the operation 308 for the image(s) of the imagery, such as for each frame in the imagery. The image labeling application 114 may store the information in the labeled data 132, which may include the imagery or may be metadata associated the imagery stored in the unlabeled imagery 104. In some embodiments, the image labeling application 114 may omit storing at least some information based on an analysis of the location information, user behavior information captured by the user behavior monitor, and/or for other reasons discussed herein. For example, the image labeling application 114 may store information associated with some, but not all, frames.

Figure 4:
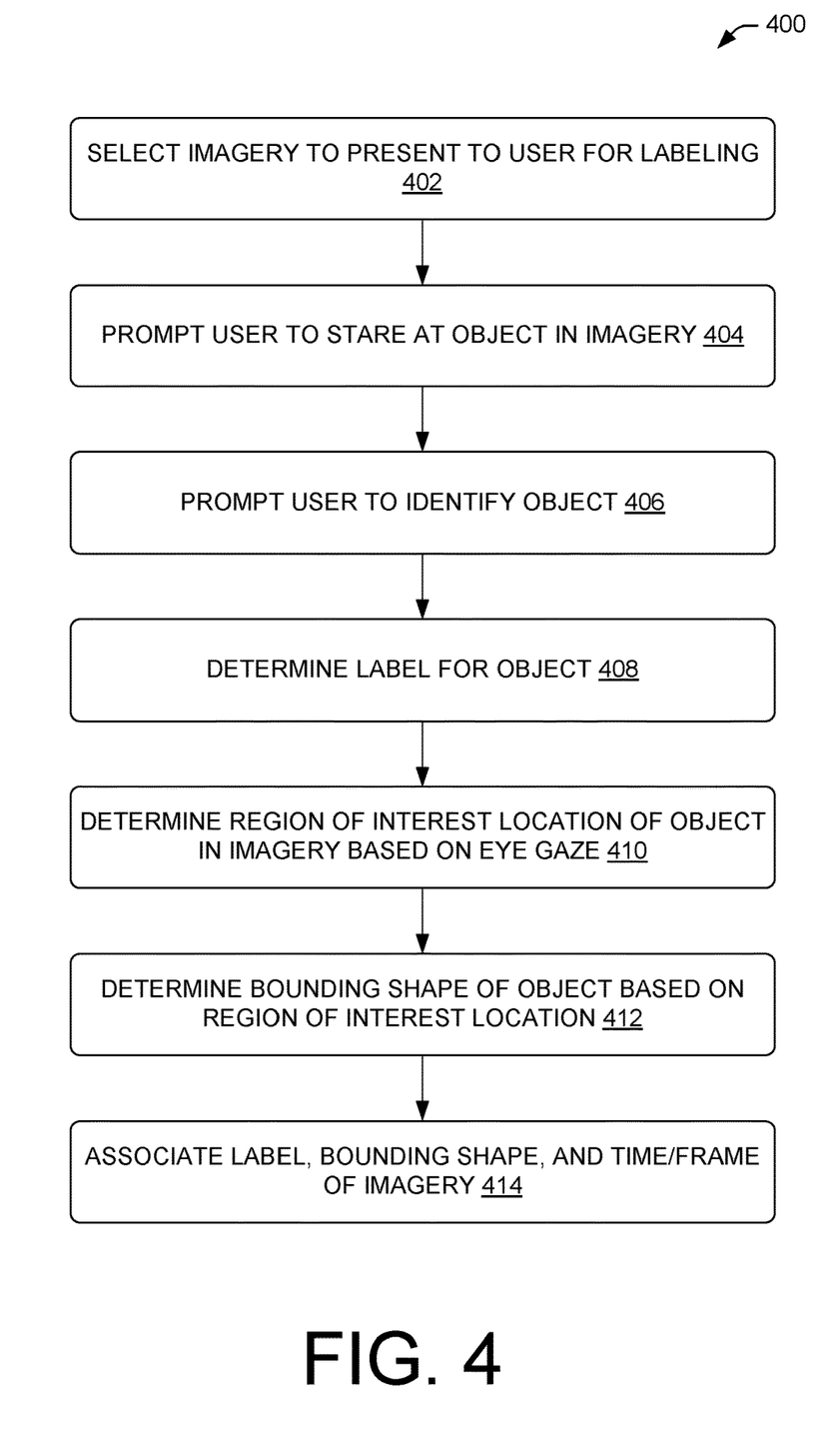
FIG. 4 is a flow diagram of an illustrative process to label location(s) associated with an object depicted in imagery based on an eye gaze of a user looking at the object and to label the object based on user input.

FIG. 4 is a flow diagram of an illustrative process 400 to label location(s) associated with an object depicted in imagery based on an eye gaze of a user looking at the object and to label the object based on user input. The process 400 is described with reference to the environment 100 and the computing architecture 200. However, the process 400 may be performed by other computing architecture and in other environments.

At 402, the imagery presenter 124 may cause a display to present imagery from the unlabeled imagery 104. For example, the imagery presenter 124 may select on image or a series of images (e.g., a video) for playback to a user that is instructed to track an object in the imagery.

At 404, the object labeler 126 may prompt the user, possibly via sound emitted from the speaker, to stare at an object in the imagery. For example, the prompt may state "look at an object that can move in the image."

At 406, the object labeler 126 may prompt the user to identify the object that the user is looking at as instructed in the operation 404. For example, the object labeler 126 may prompt the user, possibly via sound emitted from the speaker, to announce (say) the name of the object. In some instances, the object labeler 126 may supply a criteria for the object to be named by the user, such as "an object not yet named", "an object that can move", and/or by using other criteria.

At 408, the object may be labeled by the object labeler 126. For example, the speech recognition component 218 may then process the voice input from the user received from the microphone to create a label for the object (e.g., "I see a dog", etc.). In some embodiments, the speech may be parsed to identify the object name (e.g., "dog") and omit extraneous words (e.g., "I see a"). In various embodiments, the user input may be received as text, such as when the user types a name of the object, selects an object from a list, or otherwise causes selection or input of text. In some embodiments, labels may be updated to use a single word for other similar words, such as using a generic term "bird" instead of a label of a "crow" or large bird".

At 410, the eye tracking component 116 may determine a region of interest (ROI) location of the object base on a direction of a gaze of the user that is tracking the labeled object during presentation of the imagery. For example, the eye tracking component 116 may determine a pixel location, which may be the ROI location, of the imagery at a point in time or frame. The eye tracking component 116 may be synchronized with the imagery presenter to enable associating the ROI location with the point in time or frame of the imagery when the imagery is video or moving images. In some embodiments, the eye tracking component 116 may receive an input via the one or more input device(s) 214 to indicate that the user is currently looking at the object. For example, the user may be instructed to push a button or hold a button down (depressed) while staring at the object and while the object is visible in the field of view of the imagery (e.g., not obstructed by another object, etc.).

At 412, the object detection component 220 may determine that the ROI is part of a larger object, and may determine bounds for the larger object, such as by defining a bounding shape or box that at least partially surrounds the object. The object detection component 220 may determine the object location for each frame using inputs from the eye tracking component 116.

At 414, the image labeling application 114 may associate the label, the bounding shape, and the time/frame of the imagery. For example, the image labeling application 114 may store the location of the object for the image(s) of the imagery, such as for each frame in the imagery. The image labeling application 114 may store the information in the labeled data 132, which may include the imagery or may be metadata associated the imagery stored in the unlabeled imagery 104. In some embodiments, the image labeling application 114 may omit storing at least some information based on an analysis of the location information, user behavior information captured by the user behavior monitor, and/or for other reasons discussed herein. For example, the image labeling application 114 may store information associated with some, but not all, frames.

Figure 5:
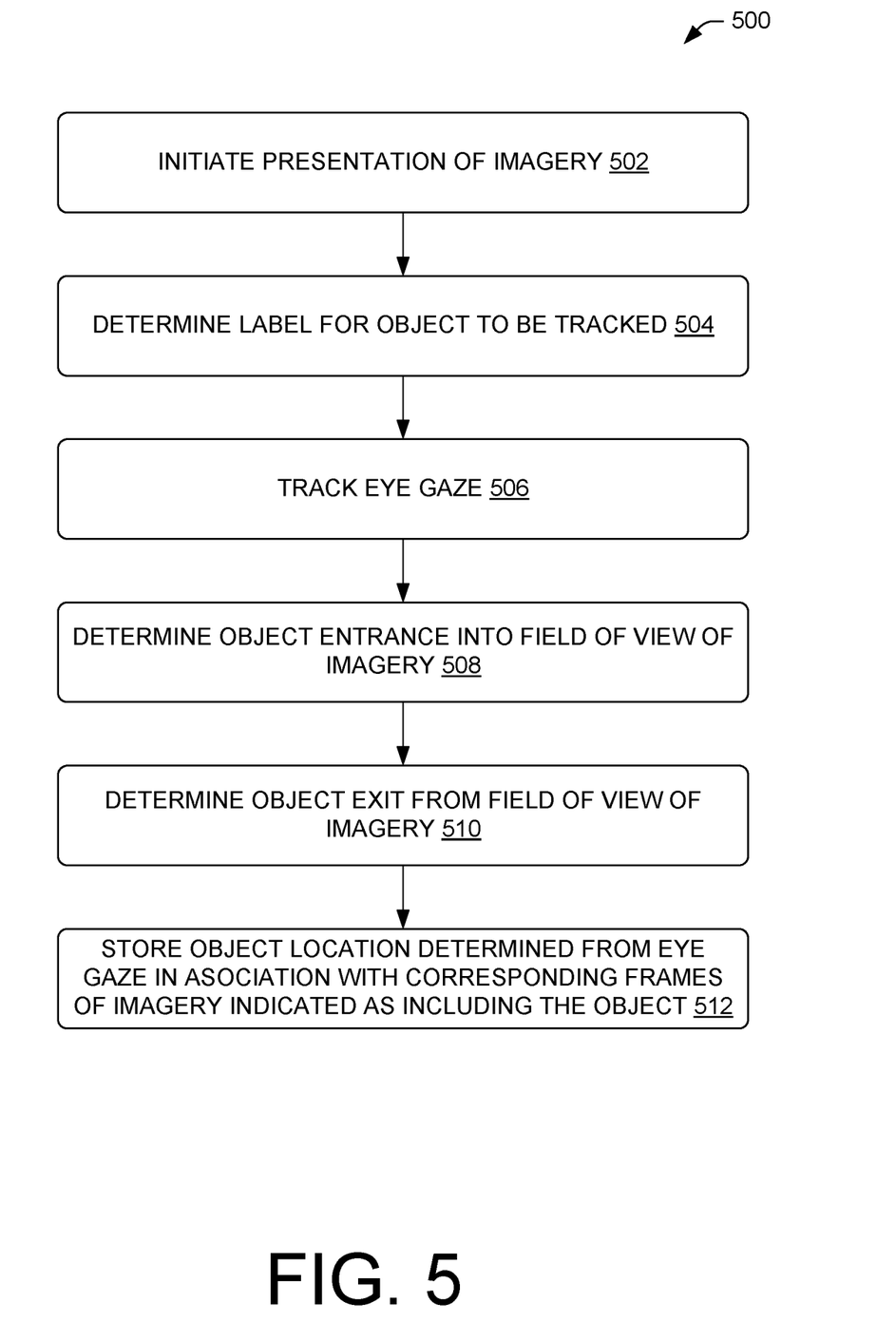
FIG. 5 is a flow diagram of an illustrative process to track movement of an object in frames of imagery as the object enters and exits a field of view associated with the imagery.

FIG. 5 is a flow diagram of an illustrative process 500 to track movement of an object in frames of imagery as the object enters and exits a field of view associated with the imagery. The process 500 is described with reference to the environment 100 and the computing architecture 200. However, the process 500 may be performed by other computing architecture and in other environments.

At 502, the imagery presenter 124 may initiate presentation of selected imagery. For example, the imagery presenter 124 may select imagery that is unlabeled or not labeled by enough users. The imagery presenter 124 may present imagery in response to an input received from the one or more input devices 214.

At 504, the object labeler 126 may determine a label for the object to be tracked by the gaze of a user. For example, the object labeler 126 may have a predetermined label to select, such as from a list of object previously identified as being in the imagery. Objects may be identified by other users (e.g., prior users that labeled the objects), via object detection algorithms, by capturing imagery of known objects (e.g., all images include a bird, etc.), and so forth. In some embodiments, the user may identify the object to create the label as described in the process 400.

At 506, the eye tracking component 116 may track a gaze of the eye to determine a location of the imagery associated with the gaze. In some embodiments, the eye tracking component may not record a location for a predetermined amount of time or a predetermined number of slides to enable the user time to find the object and begin to stare at it in the imagery depicted in the display.

At 508, the imagery labeling application 114 may determine an entrance of the object into the field of view of the imagery depicted in the display. For example, the imagery labeling application 114 may prompt a user to depress or otherwise actuate an input device when the object appears on the display of the imagery. This input may also cause the eye tracking to be performed and/or mark or otherwise designate the eye tracking data collected by the eye tracking component 116 to be used to identify a location of the object, via the ROI as discussed above.

At 510, the imagery labeling application 114 may determine an exit of the object from the field of view of the imagery depicted in the display. The exit may be caused by the object being covered or blocked from view by another object, such as an airplane being blocked by a cloud. The imagery labeling application 114 may, at an earlier time, instruct the user to release the button or depress or otherwise actuate an input device when the object appears on the display of the imagery. This input may also cause the eye tracking to be terminated and/or marked or otherwise designated as not associated with the location of the object, which is indicated as no longer visible in the imagery.

At 512, the imagery labeling application 114 may store a location of the object determined by the eye tracking of the eye gaze in association the portions of the imagery having the object. For example, frames of imagery that include the object, known by input received from the input device(s) 214 via user input, may be associated with location data derived from the eye tracking component 116. In some embodiments, the location may be a location of the object determined by the object detection component 220 that converts a ROI into a bounding shape.

Figure 6:
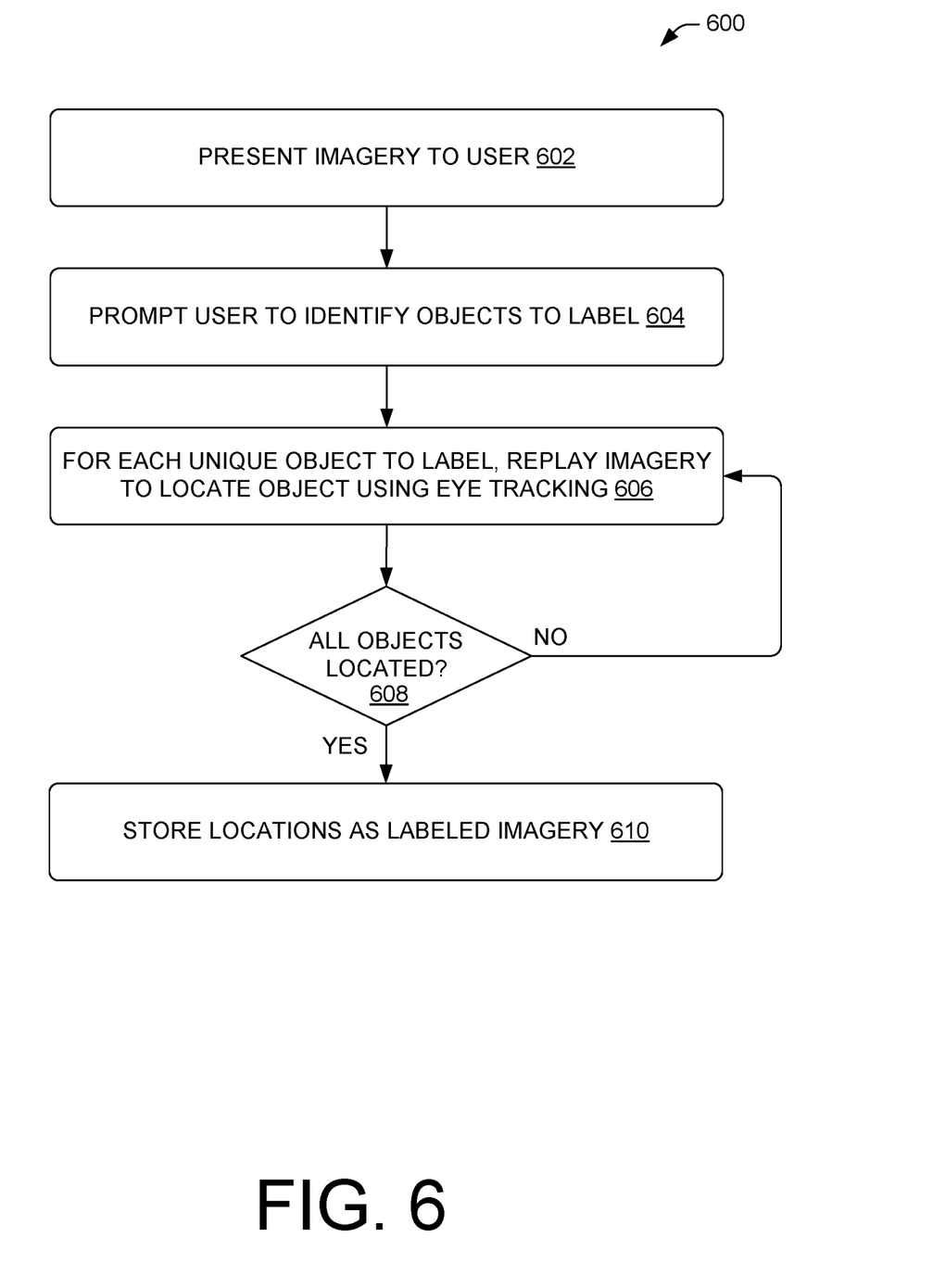
FIG. 6 is a flow diagram of an illustrative process to generate a list of objects to track in imagery, and then replay the imagery to track the objects individually.

FIG. 6 is a flow diagram of an illustrative process 600 to generate a list of objects to track in imagery, and then replay the imagery to track the objects individually. The process 600 is described with reference to the environment 100 and the computing architecture 200. However, the process 600 may be performed by other computing architecture and in other environments.

At 602, the imagery presenter 124 may select imagery to present to the user for labeling. The imagery may be selected from the unlabeled imagery 104. In some embodiments, the imagery presenter 124 may select some frames, but not all, of the frames to present to a user via the display for purposes of determining objects included in the frames. For example, every tenth frame or other intervals or random selection of frames may be used by the imagery presenter 124 for such purposes.

At 604, the object labeler 126 may prompt a user to identify objects in the frames selected in the operation 602 of the imagery. In some instances, object labeler 126 may prompt the user to identify objects not already identified in a frame or in subsequent frames. Once a user indicates that all objects are identified in a frame, possible in response to receiving an input via the one or more input device 214, the imagery presenter may present a next frame for labeling until the selected frames are viewed by the user to complete a process of identification of objects.

At 606, the imagery presenter 124 may, for each object identified in the operation 604, may replay the imagery to enable tracking of the object via the eye tracking component using one or more of the processes described herein. For example, if four objects are identified, such as "a bird", "a kite", "a dog", and "a bike" are identified, the imagery presenter 124 would replay the imagery a first time and instruct the user to track (stare at) the bird during the replay, then perform a second replay after instructing the user to track (stare at) the kite, and so forth until all four objects are located via the eye tracking component.

At 608, the imagery labeling application 114 may determine if all the objects determined by the object labeler 126 from the operation 604 have been tracked and located via the operation 606. When all objects have not been tracked (following the "no" route from the decision operation 608), then the process 600 may return to the operation 606 and repeat the operation 606 for a next object that has not been tracked or properly tracked (e.g., as determined by the validation component 224 and/or the user behavior monitor 226). When all objects have been tracked (following the "yes" route from the decision operation 608), then the process 600 may advance to an operation 610.

At 610, the image labeling application 114 may store the location of the objects determined via various performances of the operation 606 for the different objects in image(s) of the imagery, such as for each frame in the imagery. The image labeling application 114 may store the information in the labeled data 132, which may include the imagery or may be metadata associated the imagery stored in the unlabeled imagery 104. In some embodiments, the image labeling application 114 may omit storing at least some information based on an analysis of the location information, user behavior information captured by the user behavior monitor, and/or for other reasons discussed herein. For example, the image labeling application 114 may store information associated with some, but not all, frames.

Figure 7:
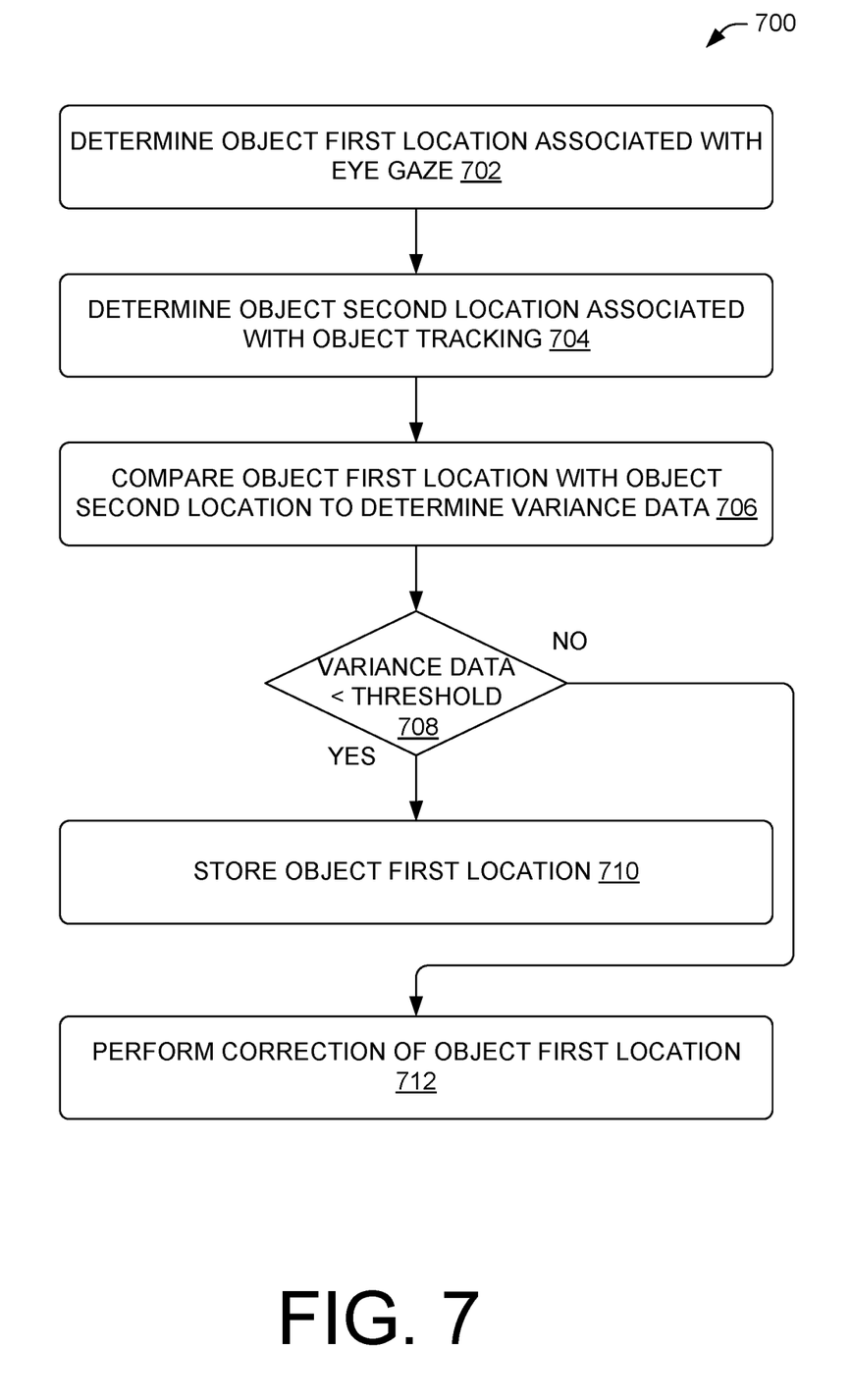
FIG. 7 is a flow diagram of an illustrative process to validate object locations determined by eye tracking.

FIG. 7 is a flow diagram of an illustrative process 700 to validate object locations determined by eye tracking. The process 700 is described with reference to the environment 100 and the computing architecture 200. However, the process 700 may be performed by other computing architecture and in other environments.

At 702, the eye tracking component 116 may determine an object first location or locations across multiple frames associated with a gaze of a user.

At 704, the object tracking component 222 may determine an object second location or locations across multiple frames associated with output of an object tracking algorithm. For example, the object tracking component 222 may analyze the same imager presented to the use to obtain the object first location(s) to determine, via one or more algorithms, movement of the object in the images of the imagery.

At 706, the validation component 224 may compare the object first location(s) with the object second location(s) to determine variance data. The comparison may determine that the user's eye at least momentarily lost focus on the object if the variance is large in some portions of the comparison. For example, the comparison may be performed on a frame by frame basis to measure a difference of a centroid of the object locations of the object first location and the object second location. A pattern than shows close correlation and then a few frames with poor correlation may indicate that the poor correlation was due to the user failing to stare at the object, sneeze, cough, or stop tracking the object temporarily for some other reason.

At 708, the validation component 224 may determine if the variance data is within a threshold variance that is permissible and indicates validity of the object first location determined by the eye tracking component 116. The threshold may be compared on a frame by frame basis or by groupings of frames to create aggregate variance data. When the variance data is less than the threshold variance (following the "yes" route from the decision operation 708), then the process 700 may advance to an operation 710.

At 710, the image labeling application 114 may store the object first location(s) of the object determined at the operation 702. The image labeling application 114 may store the information in the labeled data 132, which may include the imagery or may be metadata associated the imagery stored in the unlabeled imagery 104.

When the variance data is not less than the threshold variance (following the "no" route from the decision operation 708), then the process 700 may advance to an operation 712. At 712, the validation component 224 may perform correction of the object first location. In some embodiments, the correction may be performed by using the object second location(s) when the deviation is greater than a threshold amount (or greater than the threshold variance). In various embodiments, the imagery may be replayed to re-track the object via the user's gaze. In at least some embodiments, frames with a variance greater than the threshold may not be labeled. For example, the image labeling application 114 may omit storing at least some information based on an analysis of the location information, user behavior information captured by the user behavior monitor 226, and/or for other reasons discussed herein. For example, the image labeling application 114 may store information associated with some, but not all, frames. Other corrective actions may also be used.

Figure 8:
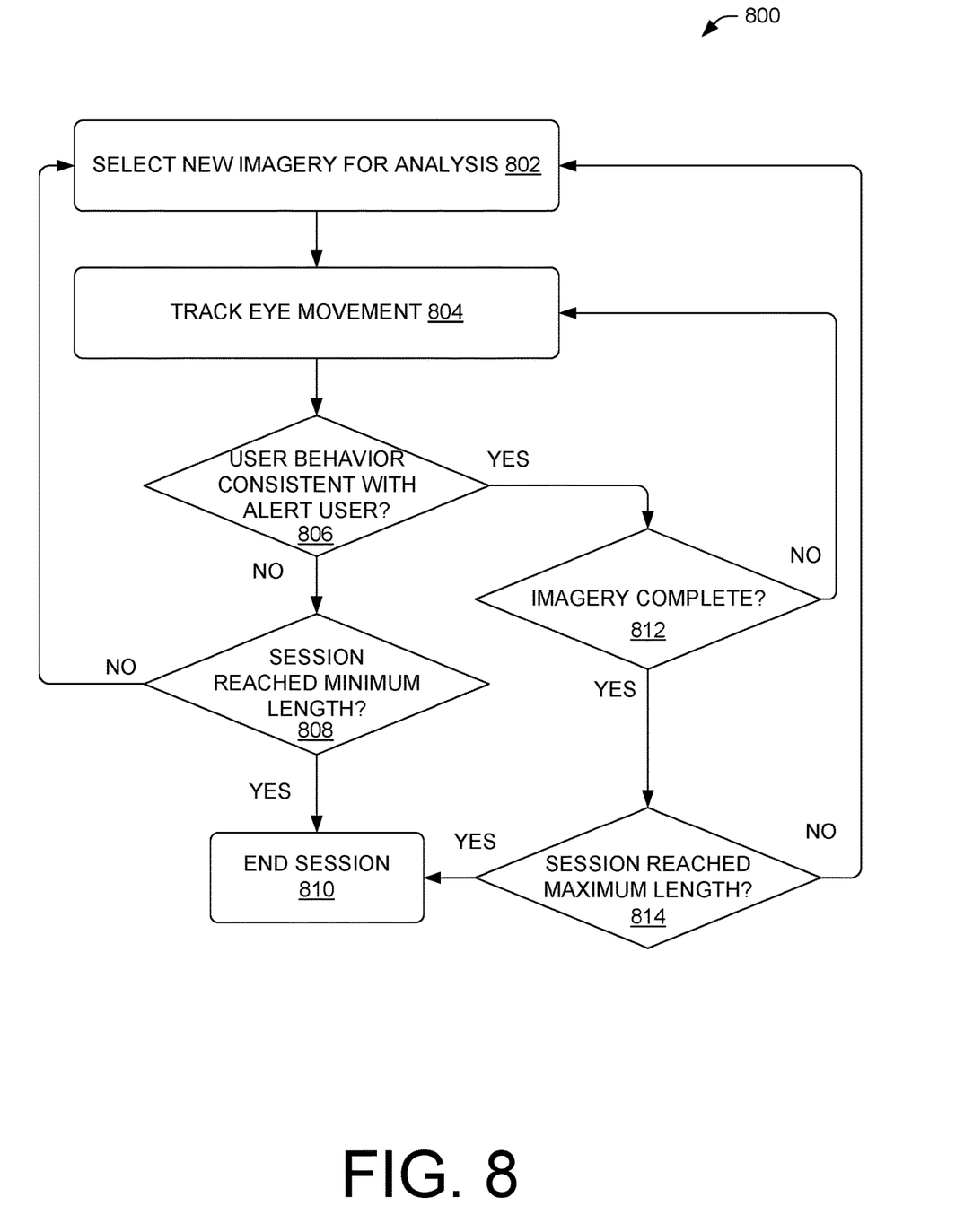
FIG. 8 is a flow diagram of an illustrative process to present imagery to a user while monitoring user eye behavior to determine when to terminate a session of labeling imagery.

FIG. 8 is a flow diagram of an illustrative process 800 to present imagery to a user while monitoring user eye behavior to determine when to terminate a session of labeling imagery. The process 800 is described with reference to the environment 100 and the computing architecture 200. However, the process 800 may be performed by other computing architecture and in other environments.

At 802, the imagery presenter 116 may select new imagery for analysis. For example, the imagery presenter 116 may select a portion of the unlabeled imagery 104 for labeling using eye tracking as discussed above.

At 804, the eye tracking component 116 may track a user's gaze. The eye tracking may determine a location of a ROI, and/or ultimately a location of the object in the imagery, as discussed above.

In accordance with some embodiments, the user behavior monitor 226 may analyze at least some of the output of the eye tracking component 116 to determine attributes of the user, such as excessive or prolonged blinking and/or other signs of sleepiness or reduced attention or alertness. The user behavior monitor 226 may detect other user behavior or actions, such as yawning, coughing, sneezing, erratic eye movement, and so forth. This eye behavior may be used below to inform further processing.

At 806, the user behavior monitor 226 may determine whether the user behavior is consistent with an alert user. For example, user movement data may be compared to various threshold data, such as blink rate, a blink duration rate, yawn rate, and so forth to determine if the user is alert (e.g., not below certain thresholds). When the user behavior monitor 226 determines that the user behavior is not consistent with an alert user (following the "no" route from the decision operation 806), then the process 800 may advance to a decision operation 808.

At 808, the imagery labeling application 114 may determine whether the session has reached a minimum length that is expected of a user to perform tracking. When the session length is within the minimum time, then the system may assume the user may become more alert by changing the imagery. When the session minimum is not reached (following the "no" route from the decision operation 808), then the process 800 may advance to the operation 802 to select new imagery for analysis. In some embodiments, the data collected in association with the prior imagery may be processed in accordance with the process 700 described above, and possibly not used to label the imagery. When the session minimum is reached (following the "yes" route from the decision operation 808), then the process 800 may advance to the operation 810. At 810, the imagery labeling application 114 may terminate the session and the user may no longer be prompted, at least for a while, to track objects as discussed herein.

When the user behavior monitor 226 determines that the eye behavior is consistent with an alert user (following the "yes" route from the decision operation 806), then the process 800 may advance to a decision operation 812. At 812, the imagery labeling application 114 may determine if the imagery presentation is complete. For example, the imagery labeling application 114 may determine whether the entire video segment of the imagery has been presented by the image presenter 124. When the imagery is not complete (following the "no" route from the decision operation 812), then the process 800 may advance to the operation 804 to continue eye tracking. When the imagery is complete (following the "yes" route from the decision operation 812), then the process 800 may advance to a decision operation 814.

At 814, the imagery labeling application 114 may determine whether a maximum session time has been reached. For example, users may label imagery for session that last a predetermined amount of time, which may be the maximum length. The minimum length discussed above with respect to the decision operation 808 may be less than the maximum length. When the imagery labeling application 114 determines that the session has not reached the maximum time (following the "no" route from the decision operation 814), then the process 800 may advance to the operation 802 to select new imagery for analysis and to continue the current session.

When the imagery labeling application 114 determines that the session has reached the maximum time (following the "yes" route from the decision operation 814), then the process 800 may advance to the operation 810 and end the session as described above.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. A system comprising:
one or more processors; and
memory to store computer: implemented instructions that, when executed, cause the one or more processors to perform acts to:
select imagery that is associated with a number of labels that is less than a labeling threshold to present to a user for labeling using eye tracking of eyes of the user;
prompt the user to stare at an object in the imagery;
prompt the user to identify a label of the object;
receive, as user input, the label of the object;
receive eye tracking data that indicates a direction of a gaze of the user staring at the object in the imagery;
determine a pixel location associated with the object based at least in part on the eye tracking data;
determining a bounding shape of the object based at least in part on the pixel location;
perform object detection on the object;
compare an output of the object detection with the bounding shape of the object to validate the pixel location; and
storing the label of the object and the bounding shape in association with the imagery.

2. The system as recited in claim 1, wherein the receiving the label includes receiving a signal from a microphone based on user speech, and wherein the computer implemented instructions cause the one or more processors to further perform acts to perform speech recognition to determine the label of the object.

3. The system as recited in claim 1, wherein the computer-implemented instructions cause the one or more processors to further perform acts to:
receive a signal from an input device; and
initiate collection of the eye tracking data in response to the signal.

4. The system as recited in claim 1, wherein the computer-implemented instructions cause the one or more processors to further perform acts to:
determine user behavior data that indicates a physical disruption associated with user;
determine object tracking data that indicates a movement of the object; and
determine that a difference between the object tracking data and the eye tracking data is less than a threshold amount.

5. The system as recited in claim 1, wherein the computer-implemented instructions cause the one or more processors to further perform acts to:
analyze the eye tracking data to determine at least one of a blink rate or a duration of a blink;
compare the blink rate or the duration of the blink to a threshold value; and
terminate a playback of the imagery based at least in part on the blink rate or the duration of the blink being equal to or greater than the threshold value.

6. The system as recited in claim 1, wherein the imagery includes a plurality of frames, and wherein the storing the label of the object and the bounding shape in association with the imagery includes storing the label of the object and the bounding shape in association with at least two frames of the plurality of frames.

7. A computer-implemented method to label an object depicted in imagery, the method comprising:
determining imagery that is associated with a number of labels that is less than a labeling threshold;
causing playback of the imagery for viewing by a user;
instructing the user to stare at the object during the playback of the imagery;
receiving eye tracking data that provides a direction of a gaze of the user;
associating the gaze of the user with a pixel location in the imagery;
receiving user input data associated with a label of the object;
associating the pixel location with the label of the object;
determining a bounding shape of the object based at least in part on the pixel location;
performing object detection on the object; and
comparing an output of the object detection with the bounding shape of the object to validate the pixel location.

8. The computer-implemented method as recited in claim 7, wherein the imagery includes a plurality of frames, and wherein the eye tracking data provides the gaze of the user that is synchronized with the playback of the imagery.

9. The computer-implemented method as recited in claim 7, further comprising terminating the playback of the imagery based at least in part on determining that a session length associated with the playback of the imagery has met or exceeded a session threshold length.

10. The computer-implemented method as recited in claim 7, further comprising storing the location of the object and the label as metadata associated with the imagery.

11. The computer-implemented method as recited in claim 7, further comprising:
instructing the user to provide the user input data to determine the label of the object; and
analyzing the user input data to determine the label for the object.

12. The computer-implemented method as recited in claim 7, further comprising:
analyzing the gaze of the user to determine an alertness value of the user; and
terminating the playback of the imagery based at least in part on the alertness value of the user being less than a threshold value.

13. The computer-implemented method as recited in claim 7, wherein the user input data is first user input data, the method further comprising:
receiving second user input data from in input device that indicates that the user is staring at the object in the imagery; and
wherein receiving the eye tracking data is based at least in part on receiving the second user input data.

14. The computer-implemented method as recited in claim 7, wherein the instructing includes causing a speaker to emit audio of a verbal instruction.

15. A system comprising:
one or more processors; and
memory to store computer-implemented instructions that, when executed, cause the one or more processors to perform acts to:
determine imagery that is associated with a number of labels that is less than a labeling threshold;

cause the imagery to be presented for labeling using eye tracking;

prompt a user to stare at an object in the imagery;

receive eye tracking data that indicates a pixel location associated with the object;

receive user input data associated with a label of the object;

associate the pixel location of the object with the label of the object;

determine a bounding shape of the object based at least in part on the pixel location;

perform object detection on the object; and compare an output of the object detection with the bounding shape of the object to validate the pixel location.

16. The system as recited in claim 15, wherein the computer-implemented instructions cause the one or more processors to further perform acts to:

receive user behavior data that indicates a physical disruption associated with the user;

determine object tracking data that indicates a movement of the object; and determine that a difference between the object tracking data and the eye tracking data is less than a threshold amount.

17. The system as recited in claim 15, wherein the computer-implemented instructions cause the one or more processors to further perform acts to:

determine a set of labels associated with the imagery, wherein the set of labels includes the label of the object.

18. The system as recited in claim 15, wherein the computer-implemented instructions cause the one or more processors to further perform acts to store the location of the object and the label as metadata associated with the imagery.

19. The system as recited in claim 15, wherein the user input data is first user input data, and wherein the computer-implemented instructions cause the one or more processors to further perform acts to receive second user input data from an input device that indicates that the user is staring at the object in the imagery.

20. The system as recited in claim 15, wherein the computer-implemented instructions cause the one or more processors to further perform acts to cause presentation of additional imagery in response to completion of labeling and tracking of the imagery.

* * * * *